United States Patent [19]
Chaudhari et al.

[11] Patent Number: 6,166,269
[45] Date of Patent: Dec. 26, 2000

[54] PROCESS FOR THE PREPARATION OF 2-PHENYL ETHANOL

[75] Inventors: Raghunath Vitthal Chaudhari; Manisha Madhukar Telkar; Chandrashekhar Vasant Rode, all of Maharashtra, India

[73] Assignee: Council of Scientific and Industrial Resesearch, Rafi Marg New Delhi, India

[21] Appl. No.: 09/257,106

[22] Filed: Feb. 24, 1999

[30] Foreign Application Priority Data

Dec. 24, 1998 [IN] India ........................ 3830/98

[51] Int. Cl.⁷ .................................................. C07C 27/00
[52] U.S. Cl. ................................................... 568/814
[58] Field of Search ............................................. 568/814

[56] References Cited

U.S. PATENT DOCUMENTS

| | | | |
|---|---|---|---|
| 1,787,205 | 12/1930 | Loehr | 568/814 |
| 2,524,096 | 10/1950 | Wood | 568/814 |
| 2,822,403 | 2/1958 | Hopff | 568/814 |
| 3,579,593 | 5/1971 | Wood | 568/814 |
| 4,064,186 | 12/1977 | Gibson | 568/814 |
| 4,943,667 | 7/1990 | Hoeldrich | 568/814 |

FOREIGN PATENT DOCUMENTS

| | | | |
|---|---|---|---|
| 512236 | 4/1995 | Canada | 568/814 |
| 3239611 | 5/1983 | Germany | 568/814 |
| 49-5932 | 1/1974 | Japan | 568/814 |
| 49-5933 | 1/1974 | Japan | 568/814 |
| 678589 | 9/1952 | United Kingdom | 568/814 |

OTHER PUBLICATIONS

Roberts, "Basic Principles of Organic Chemistry," p. 664, 1964.

*Primary Examiner*—Michael L. Shippen
*Attorney, Agent, or Firm*—Ladas & Parry

[57] ABSTRACT

The present invention provides an improved process for the preparation of 2-phenyl ethanol [CAS 60-12-8] by catalytic hydrogenation of styrene oxide [CAS 96-09-3] with supported platinum group metal catalysts in the presence of an organic as well as inorganic base as a promoter, using alcohol as a solvent. The reaction is carried out at a temperature ranging between 40–120° C. and the hydrogen pressure of 50–800 psig, under stirring conditions. After the reaction is complete, the reaction mixture is cooled to room temperature, catalyst is separated from the product by conventional methods like filtration. This invention is particularly useful as an alternative to the conventional methods like Grignard synthesis and Friedel-Craft alkylation for manufacture of 2-phenyl ethanol. This invention eliminates the handling of dangerous diethyl ether solvent, ethylene oxide and the use of $AlCl_3$ which poses serious effluent problems. The proposed invention produces 2-phenyl ethanol selectively with highest purity via the catalytic hydrogenation of styrene oxide.

4 Claims, No Drawings

PROCESS FOR THE PREPARATION OF 2-PHENYL ETHANOL

FIELD OF INVENTION

This invention relates to an improved process for the preparation of 2-phenyl ethanol (β-PEA). More particularly, it relates to a process involving hydrogenation of styrene oxide in the presence of a supported platinum group metal catalyst and organic or inorganic base as a promoter using methanol as a solvent. The catalyst system comprises one of the metals from group VIII elements such as Pt, Pd, Ni supported on carbon, silica, alumina or zeolite along with one of the bases from N- containing aromatic as well as aliphatic amines, hydroxides or carbonates of alkali metals.

BACKGROUND OF INVENTION

In the prior art, the product 2-phenyl ethanol has a variety of applications. It is a colourless liquid possessing a faint but lasting odour of rose petals. Due to this 2-phenyl ethanol is important as a fragrance chemical, used in perfumes, deodorants, soaps, detergents, etc. 2-phenyl ethanol also has bacteriostatic and antifungicidal properties. Therefore, it is used in the preparation of antiseptic creams and deodorants. This alcohol is also extensively used in the formulation of various cosmetics especially in hair shampoos and hair dyes to improve the texture and the quality of hair. 2-phenyl ethanol also has local anaesthetic properties. 2-phenyl ethanol finds applications in chemical industries, for the manufacture of important chemicals such as styrene, phenyl ethyl ester, phenyl acetaldehyde, phenyl acetic acid, benzoic acid, bis-phenyl ether, etc. As it contains aromatic ring, 2-phenyl ethanol can be nitrated, sulphonated, or chlorinated to give various substituted industrially important compounds.

Conventionally, 2-phenyl ethanol is prepared by Grignard synthesis in which chlorobenzene is converted to phenyl-magnesium chloride which reacts with ethylene oxide at 100° C. to give phenylethoxy magnesium chloride which is then decomposed with sulphuric acid to give 2-phenyl ethanol. This process involves the use of dangerous diethyl ether as a solvent. Also it is very difficult to prepare phenyl magnesium chloride in situ. However, the main problem of this process is the quality of the 2-phenyl ethanol, which is of utmost importance in the production of perfumery chemicals. The major side product obtained is biphenyl along with amounts of rearranged side products, which cannot be separated from 2-phenyl ethanol even by vacuum distillation. [Ernst T. Theimer in Fragrance Chemistry, page 271, Academic Press, New York (1982)].

Another conventional method for the preparation of 2-phenyl ethanol involves low temperature Friedel Crafts alkylation of benzene with ethylene oxide, in the presence of anhydrous aluminium chloride. The major draw back of this process is that the temperature (i.e., below 25° C.) and molar ratios of the reactants are extremely critical and it is very difficult to maintain these reaction parameters. At a slightly higher temperature coupling takes place forming a dibenzyl compound. In addition, this process is not an eco-friendly process due to the use of $AlCl_3$ as a reagent. [Richard Wilson in Kirk Other's Encyclopaedia of Chemical Technology Vol. 4, page 116, John Wiley & Sons, New York (1991)]. 2-phenyl ethanol is also prepared via reduction of styrene oxide by using different reducing agents like $LiAlH_4$, $LiAlH_4/AlCl_3$, $B_2H_6$, $LiInH_4$, $NaBH_4$, and $LiBHEt_3$. The preparation of these reagents introduces an additional step in the process and the use of reagents on a commercial scale may not be feasible. Also, the use of these reagents lead to the formation of a mixture of primary and secondary alcohol. Reduction of styrene oxide with Lithium Indium hydride has been reported to give only 33% of 2-phenyl ethanol. [Koji Tanaka et. al,. Tetrahedron letters 36, 18,3169–3172, (1995)].

Catalytic hydrogenation of styrene oxide, using both homogeneous and heterogeneous catalysts have also been reported. The use of homogeneous catalysts poses a serious problem of separation and recovery of pure PEA. Various patents have made attempts to increase the selectivity of PEA using heterogeneous catalysts. Among the heterogeneous catalysts, Raney nickel was generally used alone or along with various promoters. According to U.S. Pat. No. 2,822,403, catalytic hydrogenation of styrene oxide was carried out in the presence of water. Use of emiulsifying or dispersing agents was recommended to achieve the required yield. In this process the catalyst used was a combination of Raney nickel and other hydrogenating catalyst like Cobalt, Platinum and Palladium. However, this process has several disadvantages. For instance, expensive and time consuming distillation is required to remove large amounts of water. Solvent extraction and salting out procedure are rendered difficult due to the presence of emulsifying agents. The greatest disadvantage of the process of this patent is the formation of large quantities of ethyl benzene, which destroys the aroma of PEA. British Patent No. 760.768 describes a similar catalytic hydrogenation of a suspension of styrene oxide and water. However, this patent suggests the use of Raney nickel alone instead of a combination of Raney nickel and Palladium. This process also suffers from the previously discussed disadvantages. U.S. Pat No. 3, 579, 593, which is equivalent to DE 1,918,852 describes hydrogenation of styrene oxide, again using a combination of Raney nickel and Palladium. Specific metal compositions of Raney nickel and Palladium are disclosed. According to this patent, neither of the catalysts alone, gives good results. Using Raney nickel alone, 10% ethyl benzene is formed which totally destroys the aroma of PEA, while use of Palladium alone as a catalyst produces 11% acetaldehyde. Besides this, PEA formation is only 85%. In Patent No. DE 3,239,611, PEA selectivity was as high as 97% by a two step hydrogenation of styrene oxide and using a combination of acetic acid and triethyl amine as a promoter system.

Hydrogenation of styrene oxide containing <0.5% chloro derivatives of styrene oxide was also carried out in a fixed bed reactor using $Ni/Al_2O_3$ as a catalyst at hydrogen pressure <2 MPa and temperature 338–353° K. The resulting crude product contained 66% 2-phenyl ethanol, styrene oxide 6.7%, ethyl benzene 23.5%, toluene 1.6%. [Patent Szydlowska Tueno, Celler, Pol. PL 137,142 (1987)].

Recently, gas phase hydrogenation of styrene oxide over pentasile type zeolite phosphate doped with a metal as a catalyst to give 2-phenyl ethanol has been reported. The styrene oxide and hydrogen were passed through a tube reactor packed with catalyst prepared by calcining a borosilicate with $Cu(NO_3)_2$ at 540° C. to give 78.4% 2-phenyl ethanol. [Holderich Wolfgang, Goelz Narbert, Hupfer Leopold (BASF) Ger offen DE 3,801,106,(1989)].

The above-mentioned process suffers from various drawbacks such as use of hazardous chemicals, separation of the catalyst used, separation of the product and the selectivity.

OBJECTS OF THE INVENTION

The main object of the present invention therefore is to provide a process for the preparation of 2-phenyl ethanol, which avoids use of hazardous chemicals like ethylene oxide, Aluminium chloride, and Raney nickel.

Another object is to provide a process using a supported catalyst, which could be easily separated from the reaction mixture.

Still another object is to provide a process with almost total selectivity for the production of 2-phenyl ethanol.

The process of the present invention also avoids the use of hazardous material such as diethyl ether, ethylene oxide, and $AlCl_3$, of the conventional process. The present process gives >99.5% conversion of styrene oxide with 99.9% selectivity to 2-phenyl ethanol at milder reaction conditions. Since a very high selectivity of PEA is achieved by this process, it requires merely the filtration of catalyst and distillation steps to obtain 2-phenyl ethanol of the perfumery grade purity.

SUMMARY OF THE INVENTION

The present invention provides an improved process for the preparation of 2-phenyl ethanol [CAS 60-12-8] by catalytic hydrogenation of styrene oxide [CAS 96-09-3] with supported platinum group metal catalysts in the presence of an organic as well as inorganic base as a promoter, using alcohol as a solvent. The reaction is carried out at a temperature ranging between 40–120° C. and the hydrogen pressure of 50–800 psig, under stirring conditions. After the reaction is complete, the reaction mixture is cooled to room temperature, and the catalyst is separated from the product by conventional methods like filtration. This invention is particularly useful as an alternative to the conventional methods like Grignard synthesis and Friedel-Craft alkylation for manufacture of 2-phenyl ethanol. This invention eliminates the handling of dangerous diethyl ether solvent, ethylene oxide and the use of $AlCl_3$, which poses serious effluent problems. The proposed invention produces 2-phenyl ethanol selectively with highest purity via the catalytic hydrogenation of styrene oxide.

DETAILED DESCRIPTION OF THE INVENTION

Accordingly, the present invention provides an improved process for preparation of 2-phenyl ethanol which comprises hydrogenating the solution of styrene oxide in an organic solvent, under stirring conditions, over a supported platinum group metal catalyst in the presence of a promoter, at temperature ranging between 40–120° C., terminating the reaction, cooling the reaction mixture to room temperature, and separating catalyst by conventional methods and the isolating the product by distllation. As the promoters added are basic in nature, the pH of the reaction mixture plays an important role in deciding the selectivity of the PEA. Using promoters such as NaOH, the pH of the reaction mixture is maintained at 12 to 13. At this pH the opening of the epoxide is fast which gives diol as an intermediate. This diol on hydrogenation with supported platinum group catalyst gives PEA selectivity. As the promoter and the catalyst are present in the same medium, it is not necessary to separate the intermediate formed. The intermediate formed is reduced immediately to PEA. Therefore, high selectivity of PEA is obtained in one step by simply filtering the catalyst. In this developed process, using NaOH as promoter, the selectivity obtained is 99.9%, i.e., almost 100%.

In a preferred embodiment of the present invention, the supported catalyst is selected from platinum group metals like platinum, palladium, nickel on various supports such as carbon, alumina, silica and zeolites.

In another embodiment the organic solvents used for preparing the solution of styrene oxide are aliphatic or aromatic hydrocarbon solvents selected from the group consisting of hexane, 1–4 dioxane, benzene, toluene, ethyl acetate, methanol, ethanol or higher alcohols.

In yet another embodiment the promoter employed is an organic base selected from the group consisting of pyridine, quinoline, triethylamine, diethyl amine, and dimethyl amine, or inorganic base, such as sodium hydroxide, potassium hydroxide, sodium carbonate, or potassium carbonate.

In a further embodiment, the pH of the reaction mixture is in the range of 12 to 13. This increases the selectivity of PEA from 51% to almost 100%. (99%) In still another embodiment the hydrogen pressure is in the range of 50–800 psig. In a feature of the present invention the supported platinum group metal catalyst is prepared as per the procedure given by Mozingo, R.;org. Syn. Coll. Vol. $3_{rd}$ Ed. 1956.

The process of the invention is described in detail in the following illustrative but non-limitative examples:

EXAMPLE 1

This example illustrates the use of conventional Pd/C catalyst for conversion of styrene oxide to 2-phenyl ethanol without using promoter. In a typical experiment, styrene oxide 5 cms (0.04166 moles), 95 gms of methanol as a solvent, 0.075 gms of 1% Pd/C were charged in a reactor. This reaction was carried out without a promoter at 40° C. and under hydrogen pressure of 300 psig in a 300 cm³ autoclave equipped with magnetic drive for agitation. After the reaction was complete, the reactor was cooled below ambient temperature and the contents were discharged. The GC analysis of the reaction mixture showed complete conversion of styrene oxide while the selectivity of 2-phenyl ethanol obtained was 51%. The major side products obtained were 2-methoxy ethyl benzene and 1,2 dimethoxy ethyl benzene. The reactant and products were analysed and confirmed by GC, GCIR, and GCMS.

EXAMPLE 2

This example illustrates the effect of solvent without using promoter. In a typical experiment, styrene oxide 5 gms (0.04166 moles), 95 gms of hexane as a solvent, 0.075 gms of 1% Pd/C were charged in a reactor. This reaction was carried out without a promoter at 40° C. and under hydrogen pressure of 300 psig in a 300 cm³ autoclave equipped with magnetic drive for agitation. After the reaction was complete, the reactor was cooled below ambient temperature and the contents were discharged. The GC analysis of the reaction mixture showed 73% conversion of styrene oxide while the selectivity of 2-phenyl ethanol obtained was 99.1%. The reactant and products were analysed and confirmed by GC, GCIR, and GCMS.

EXAMPLE 3

This example illustrates the effect of solvent without using promoter. In a typical experiment, styrene oxide 5 gms (0.04166 moles), 95 gms of 1–4 dioxane as a solvent, 0.075 gms of 1% Pd/C were charged in a reactor. This reaction was carried out without a promoter at 40° C. and under hydrogen pressure of 300 psig in a 300 cm³ autoclave equipped with magnetic drive for agitation. After the reaction was complete, the reactor was cooled below ambient temperature and the contents were discharged. The GC analysis of the reaction mixture showed 30% conversion of styrene oxide while the selectivity of 2-phenyl ethanol obtained was 99.31%. The reactant and products were analysed and confirmed by GC, GCIR, and GCMS.

EXAMPLE 4

This example illustrates the effect of solvent using NaOH as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms NaOH as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed complete conversion of styrene oxide while the selectivity of 2-phenyl ethanol obtained was 99.9%. The reactant and products were analysed and confirmed by GC, GCIR, and GCMS.

EXAMPLE 5

This example illustrates the effect of low pressure using NaOH as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms NaOH as a promoter at 40° C. and under hydrogen pressure of 100 psig in a 300 cm$^3$ autoclave equipped with magnetic drive for agitation. After the reaction was complete, the reactor was cooled below ambient temperature and the contents were discharged. The GC analysis of the reaction mixture showed 90% conversion of styrene oxide while the selectivity of 2-phenyl ethanol obtained was 99.0%. The reactant and products were analysed and confirmed by GC, GCIR, and GCMS.

EXAMPLE 6

This example illustrates the effect of temperature using NaOH as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms NaOH as a promoter at 50° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed complete conversion of styrene oxide while the selectivity of 2-phenyl ethanol obtained was 99.0%. The reactant and products were analysed and confirmed by GC, GCIR, and GCMS.

EXAMPLE 7

This example illustrates the effect of Na$_2$CO$_3$ as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms Na$_2$CO$_3$ as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed 45% conversion of styrene oxide while the selectivity of 2-phenyl ethanol obtained was 97.0%. The reactant and products were analysed and confirmed by GC, GCIR, and GCMS.

EXAMPLE 8

This example illustrates the effect of pyridine as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms pyridine as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed 64% conversion of styrene oxide while the selectivity of 2-phenyl ethanol obtained was 99.69%. The reactant and products were analysed and confirmed by GC, GCIR, and GCMS.

EXAMPLE 9

This example illustrates the effect of quinoline as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms quinoline as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed complete conversion of styrene oxide while the selectivity of 2-phenyl ethanol obtained was 99.65%. The major side product obtained was 1-methoxy ethyl benzene. The reactant and products were confirmed and analysed by (GC, GCIR, and GCMS.

EXAMPLE 10

This example illustrates the effect of tri ethyl amine as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms tri ethyl amine as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed 70% conversion of styrene oxide while the selectivity of 2-phenyl ethanol obtained was 98.98%. The other side product obtained was ethyl benzene, analysed and confirmed GCIR, and GCMS.

EXAMPLE 11

This example illustrates the effect of di ethyl amine as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms di ethyl amine as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed 47.59% conversion of styrene oxide while the selectivity of 2-phenyl ethanol obtained was 99.0%. The reactant and product were analysed and confirmed by GC, GCIR, and GCMS.

EXAMPLE 12

This example illustrates the effect of di methyl amine as a promoter. In a typical experiment, styrene oxide 5 gms (0.04166 moles), 95 gms of methanol as a solvent, 0.075 gms of 1% Pd/C were charged in a reactor. This reaction was carried out with 0.13 gms di methyl amine as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed 55.02% conversion of styrene oxide while the selectivity of 2-phenyl ethanol obtained was 99.0%. The reactant and products were analysed and confirmed by GC, GCIR, GCMS

EXAMPLE 13

This example illustrates the effect of support while using NaOH as a promoter. In a typical experiment, styrene oxide 5 gms (0.04166 moles), 95 gms of methanol as a solvent, 0.075 gms of 1% Pd/Al$_2$O$_3$ were charged in a reactor. This reaction was carried out with 0.13 gms NaOH as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed 42% conversion of styrene oxide while the selectivity of 2-phenyl ethanol obtained was 99.98%. The reactant and products were analysed and confirmed by GC, GCIR, and GCMS.

EXAMPLE 14

This example illustrates the catalytic effect using NaOH as a promoter. In a typical experiment, styrene oxide 20 gms, 80 gms of methanol as a solvent, 0.1035 gms of 1% Pt/C were charged in a reactor. This reaction was carried out with 0.13 gms NaOH as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed 70% conversion of styrene oxide while the selectivity of 2-phenyl ethanol obtained was 88%. The other side products obtained were 2-methoxy ethyl benzene and 1,2 dimethoxy ethyl benzene. The reactant and products were analysed and confirmed by GC, GCIR, and GCMS.

EXAMPLE 15

This example illustrates the catalytic effect using NaOH as a promoter. In a typical experiment, styrene oxide 5 gms (0.04166 moles), 95 gms of methanol as a solvent, 0.075 gms of 10% Ni/C were charged in a reactor. This reaction was carried out with 0.13 gms NaOH as a promoter at 40° C. and under hydrogen pressure of 300 psig in a 300 cm$^3$ autoclave equipped with magnetic drive for agitation. After the reaction was complete, the reactor was cooled below ambient temperature and the contents were discharged. The GC analysis of the reaction mixture showed 60% conversion of styrene oxide while the selectivity of 2-phenyl ethanol obtained was 85%. The other side products obtained were 2 methoxy ethyl benzene and 1,2-dimethoxy ethyl benzene. The reactant and products were analysed and confirmed by GC, GCIR, and GCMS.

The present invention gives following advantages over any known process:

selective catalytic hydrogenation of styrene oxide to 2-phenyl ethanol is achieved using 1% pd/c and naoh Under milder reaction conditions.

Easy separation of the product 2-phenyl ethanol in the pure form.

The catalyst can be easily separated form the reaction mixture.

We claim:

1. A process for preparation of 2-phenyl ethanol which comprises the steps of hydrogenating a solution of styrene oxide in an organic solvent, under stirring conditions, over a supported platinum group metal catalyst in the presence of sodium hydroxide as a promoter, at a pH in the range of 12 to 13 and at a temperature ranging between 40–120° C., terminating the reaction, cooling the reaction mixture to room temperature, separating the catalyst and isolating the product by distillation.

2. A process as claimed in claim 1 wherein, the supported catalyst is a platinum group metal selected from the group consisting of platinum, palladium, and nickel on supports selected from the group consisting of carbon, alumina, silica and zeolites.

3. A process as claimed in claim 1 wherein, the organic solvents used for preparing the solution of styrene oxide comprise aliphatic or aromatic hydrocarbon solvents selected from the group consisting of hexane, 1–4 dioxane, benzene, tolunene, ethyl acetate, methanol, ethanol and higher alcohols.

4. A process as claimed in claim 1 wherein, the hydrogen pressure is in the range of 50–800 psig.

* * * * *